United States Patent [19]

Oxman et al.

[11] Patent Number: 5,709,548
[45] Date of Patent: Jan. 20, 1998

[54] DENTAL CROWN LINER COMPOSITION AND METHODS OF PREPARING PROVISIONAL APPLICATIONS

[75] Inventors: Joel D. Oxman, Minneapolis; Scott E. Anderson, Vadnais Heights, both of Minn.

[73] Assignee: Minnesota Mining and Manufacturing Company, St. Paul, Minn.

[21] Appl. No.: 801,288

[22] Filed: Feb. 18, 1997

Related U.S. Application Data

[60] Continuation of Ser. No. 445,147, May 19, 1995, abandoned, which is a division of Ser. No. 263,551, Jun. 22, 1994, abandoned, which is a continuation-in-part of Ser. No. 137,584, Oct. 15, 1993, Pat. No. 5,403,183, which is a continuation of Ser. No. 484,695, Feb. 23, 1990, abandoned.

[51] Int. Cl.$^6$ .................. C08G 63/08; A61C 5/08
[52] U.S. Cl. .................. 433/218; 433/222.1; 433/223; 433/40; 522/93; 522/142; 522/908; 523/116
[58] Field of Search .................. 433/218, 222.1, 433/223, 40, 214; 522/90, 93, 908, 142; 523/116

[56] References Cited

U.S. PATENT DOCUMENTS

| | | |
|---|---|---|
| 1,763,553 | 3/1929 | Dennis . |
| 2,404,683 | 6/1946 | Barishman . |
| 2,705,492 | 4/1955 | Chandler . |
| 2,985,961 | 5/1961 | Schwartz .................. 32/2 |
| 3,124,129 | 3/1964 | Grossberg .................. 128/136 |
| 3,333,582 | 8/1967 | Cathcart .................. 128/136 |
| 3,382,202 | 5/1968 | Forrester et al. .................. 260/32.6 |
| 3,427,161 | 2/1969 | Laridon et al. .................. 96/35.1 |
| 3,647,498 | 3/1972 | Dougherty .................. 433/218 |
| 3,756,827 | 9/1973 | Chang et al. .................. 96/86 |
| 3,759,807 | 9/1973 | Osborn et al. .................. 204/159.23 |
| 3,767,627 | 10/1973 | Schoen .................. 260/78.3 |
| 3,923,729 | 12/1975 | Clendinning et al. .................. 260/40 |
| 4,059,715 | 11/1977 | Pletcher .................. 428/349 |
| 4,071,424 | 1/1978 | Dart et al. .................. 204/159.15 |
| 4,182,829 | 1/1980 | Walkowiak et al. .................. 528/75 |
| 4,227,877 | 10/1980 | Tureaud et al. .................. 433/37 |
| 4,240,415 | 12/1980 | Wartman .................. 128/90 |
| 4,327,013 | 4/1982 | Peters .................. 524/538 |
| 4,330,283 | 5/1982 | Michl et al. .................. 433/218 |
| 4,361,528 | 11/1982 | Ginsburg et al. .................. 264/168 |
| 4,413,979 | 11/1983 | Ginsburg et al. .................. 433/41 |
| 4,433,958 | 2/1984 | Fellman et al. .................. 433/219 |
| 4,445,854 | 5/1984 | Bekey et al. .................. 433/37 |
| 4,483,333 | 11/1984 | Wartman .................. 128/90 |
| 4,491,453 | 1/1985 | Koblitz et al. .................. 523/115 |
| 4,552,906 | 11/1985 | Podszun et al. .................. 523/115 |
| 4,569,342 | 2/1986 | Von Nostitz .................. 128/136 |
| 4,642,126 | 2/1987 | Zador et al. .................. 51/295 |
| 4,657,509 | 4/1987 | Morris . |
| 4,659,786 | 4/1987 | Kawakami et al. .................. 525/415 |
| 4,678,435 | 7/1987 | Long .................. 433/218 |
| 4,740,245 | 4/1988 | Futami et al. .................. 106/35 |
| 4,759,798 | 7/1988 | von Nostitz .................. 523/115 |
| 4,761,136 | 8/1988 | Madhaven et al. .................. 522/90 |
| 4,768,951 | 9/1988 | Abiru et al. .................. 433/48 |
| 4,776,792 | 10/1988 | Wagner et al. .................. 433/71 |
| 4,787,850 | 11/1988 | Michl et al. .................. 523/115 |
| 4,813,875 | 3/1989 | Hare .................. 433/214 |
| 4,828,583 | 5/1989 | Oxman et al. .................. 51/295 |
| 4,835,203 | 5/1989 | Sieverding .................. 524/277 |
| 4,859,742 | 8/1989 | Pattein et al. .................. 525/131 |
| 4,867,680 | 9/1989 | Hare et al. .................. 433/37 |
| 4,912,174 | 3/1990 | Grouiller .................. 525/415 |
| 4,952,614 | 8/1990 | Reiners et al. .................. 523/115 |
| 5,011,407 | 4/1991 | Pelerin .................. 433/71 |
| 5,028,667 | 7/1991 | McLain et al. .................. 525/415 |
| 5,066,231 | 11/1991 | Oxman et al. .................. 433/48 |
| 5,403,188 | 4/1995 | Oxman et al. .................. 433/218 |
| 5,415,544 | 5/1995 | Oxman et al. .................. 433/214 |

FOREIGN PATENT DOCUMENTS

| | | |
|---|---|---|
| 150952 | 2/1976 | European Pat. Off. . |
| 0 087 329 | 8/1983 | European Pat. Off. . |
| 0096020 | 12/1983 | European Pat. Off. . |
| 0173085 | 7/1984 | European Pat. Off. . |
| 0 443 269 | 10/1993 | European Pat. Off. . |
| 2078675 | 11/1971 | France . |
| 3810907 | 10/1988 | Germany . |
| 63-270759 | 5/1986 | Japan . |
| 63-171554 | 6/1987 | Japan . |
| 1304112 | 3/1975 | United Kingdom . |
| 83/02898 | 9/1983 | WIPO . |
| WO-9014052 | 11/1990 | WIPO . |
| 91/12776 | 9/1991 | WIPO . |
| WO 94/07429 | 4/1994 | WIPO .................. A61C 13/00 |

OTHER PUBLICATIONS

TONE$^R$ P-300 and P-700 High Molecular Weight Caporlactone Polymers (1988 pro literature of Union Carbide Corp.).

Chem. Ab. 95:225704U, Mar., 1980.

AQUERON™ bite registration sticks and custom tray material E.M. Natt Ltd., Dec. 8, 1989.

Patent Abstract of Japanese Publication No. JP-A-1269613, published Oct. 26, 1989.

Advertisement "Unifast LC" light cured acrylic resin by GC Int'l Corp.

Product Brochure "GC Unifast LC" Light quick-curing acrylic resin. by GC Int'l Corp.

*Primary Examiner*—Susan W. Berman
*Attorney, Agent, or Firm*—Gary L. Griswold; Walter N. Kirn; Dale A. Bjorkman

[57] ABSTRACT

Thermoplastic compositions are used for the fabrication of provisional (i.e., temporary) prosthetic devices, especially for the fabrication of crowns and bridges, and as liners for crowns. Preferably, the thermoplastic compositions comprise free-radically polymerizable functionality so that the material can be polymerized after being shaped to a desired configuration.

28 Claims, 3 Drawing Sheets

DENTAL CROWN LINER COMPOSITION AND METHODS OF PREPARING PROVISIONAL APPLICATIONS

CROSS-REFERENCE TO RELATED APPLICATION

This application is a continuation application of U.S. Ser. No. 08/445,147, filed May 19, 1995, now abandoned, which is a divisional application of U.S. Ser. No. 08/263,551, filed Jun. 22, 1994, now abandoned, which is a continuation-in-part of U.S. patent application Ser. No. 08/137,584, filed Oct. 15, 1993, now U.S. Pat. No. 5,403,188, which in turn is a continuation of U.S. patent application Ser. No. 07/484,695, filed Feb. 23, 1990, now abandoned.

FIELD OF THE INVENTION

This invention relates to thermoplastic molding compositions. It also relates to dental impression taking, to the manufacture of provisional oral prosthetic devices such as dentures, inlays, onlays, veneers, crowns and bridges, liners for crowns and to general-purpose modelmaking.

BACKGROUND OF THE INVENTION

Currently available materials for fabrication of provisional restorations include acrylics and resin based composites. Acrylics are low in cost, but are odoriferous, have low tear resistance, a weak rubbery state and exhibit undesirable shrinkage and exotherm properties. Resin based composites characteristically are expensive, tend to be brittle and are difficult to remove from undercuts and to trim. Powder:liquid and paste:paste systems, whether acrylic or resin based composite, require mixing before use which often results in undesirable air incorporation. Many of the systems also involve numerous time consuming steps and provide limited operator control over the system.

High molecular weight poly (epsilon caprolactone) (also known as "polycaprolactone") has been used as a thermoplastic molding compound for general purpose modelmaking and dentistry. References describing polycaprolactone molding compositions include U.S. Pat. No. 4,835,203, Kokai (Japanese Published Pat. Appl.) Nos. 63-171554 and 63-270759, and *TONE® POLYMERS P-300 AND P-700 High Molecular Weight Caprolactone Polymers* (1988 product literature of Union Carbide Corp.). The polycaprolactone described in Kokai No. 63-171554 is said to be polymerized in the presence of a small amount of epoxy resin, which is said to improve the hydrolysis resistance of the polycaprolactone.

Deldent Dental Supplies Co., Ltd. sells a heat-softenable custom tray material referred to as the "formable base impression" or "FBI" denture tray system. The FBI tray is immersed in hot water to soften the tray, placed in a patient's mouth while warm and shaped to conform to the patient's arch. The FBI tray is said to return to its original configuration if immersed again in hot water.

U.S. Pat. Nos. 4,240,415 and 4,483,333 describe radiation-crosslinked polycaprolactone orthopedic casts. The patents refer to the possible inclusion of "chemicals containing two or more double bonds in each molecule". The casts are radiation-crosslinked using several 5 megarad exposures in an electron beam apparatus.

SUMMARY OF THE INVENTION

The present invention provides a composition useful for lining crowns and for fabrication of provisional restorations. The composition comprises a thermoplastic material that is solid at 38° C. and has a melting or softening point that comfortably can be withstood by oral tissues.

The invention also provides methods for making provisional dental restorations. One such method comprises the steps of (a) applying a molten or softened thermoplastic material onto a prepared dental area, the material being solid at 38° C. and having a melting or softening point that comfortably can be withstood by oral tissues, (b) shaping the material over the area to fully cover the area and form a prosthesis, and (c) cooling the material so that it solidifies.

Another method for making a provisional restoration comprises the steps of (a) taking an impression of an unprepared dental area, (b) applying a molten or softened thermoplastic material to the impression at the site of a prepared dental area, the material being solid at 38° C. and having a melting or softening point that comfortably can be withstood by oral tissues, (c) placing the impression having the material prepared in step (b) on the prepared area in a patient's mouth to form a prosthesis, and (d) cooling the composition so that it solidifies.

Yet another method for fabricating a provisional restoration comprises the steps of (a) taking an impression of an unprepared dental area, (b) taking an impression of a prepared dental area, (c) making a model from the impression of step (b), (d) applying a molten or softened thermoplastic material to the impression of step (a), the material being solid at 38° C., (e) placing the impression having the material prepared in step (d) onto the model of step (c) to form a prosthesis, and (f) cooling the material so that it solidifies.

Still another method for making a provisional restoration comprises the steps of (a) taking an impression of an unprepared dental area, (b) making a model from the impression of step (a), (c) making a vacuum formed shell from the model of step (b), (d) applying a molten or softened thermoplastic material to the vacuum formed shell, the material being solid at 38° C. (e) placing the vacuum formed shell having the material on the prepared area in the patient's mouth to form a prosthesis, and (f) cooling the material so that it solidifies.

DETAILED DESCRIPTION

The thermoplastic molding composition of the invention has particular utility for the fabrication of provisional (i.e., temporary) prosthetic devices, especially for the fabrication of crowns and bridges. The composition may be used for single as well as multiple unit restorations. The provisional prosthesis functions as a temporary restoration from the time the dental area is prepared for restorative procedures until the final prosthesis is cemented in place in the mouth. The provisional prosthesis is generally in the patient's mouth for several weeks while the permanent prosthesis is fabricated. The primary purpose of the provisional prosthesis is to protect the tooth and gingival tissues and stabilize mobile teeth while providing comfort, function and esthetics to the patient.

The thermoplastic molding composition of the invention may be used to prepare provisional prosthetic devices using either the direct or the indirect method of fabrication. Either method entails preparation of the dental area for restorative procedures. Preparation generally involves removal of tooth structure, but in instances where tooth structure is missing, a replacement structure, usually a wax model or prefabricated prosthesis form, is inserted in the requisite position prior to taking of an impression. The direct method of making a provisional prosthetic device is characterized by fabrication of the prosthetic device in the mouth of the patient whereas the indirect method is characterized by fabrication of the prosthetic device outside of the patient's mouth.

One type of direct method of fabrication involves taking an impression of a dental area prior to preparation of the area for restorative procedures. The tray containing impression material is maintained in place until the impression material has hardened. The molten or softened thermoplastic molding composition of the invention is transferred into the impression at the site of the prepared area. The impression containing the thermoplastic composition is then placed directly on the prepared area in the patient's mouth to form the prosthesis.

Alternatively, the direct method of fabrication may involve utilization of a metal or plastic preformed crown shell as the impression. Using this technique, a crown shell is partially or totally filled with the molten or softened thermoplastic molding composition of the invention. The filled crown shell is then placed over the prepared tooth to form a crown. The crown shell containing the thermoplastic composition is cooled so that the thermoplastic composition solidifies. Following cooling, the thermoplastic composition may be polymerized and the crown shell is then removed from the underlying solidified thermoplastic composition. However, when a transparent plastic preformed crown shell is utilized, the thermoplastic composition may be polymerized through the crown shell by irradiation with a curing light and the combination of the shell and the thermoplastic composition may serve as the provisional prosthesis.

Another type of direct method of fabrication involves making a model from the impression of the unprepared area and making a vacuum formed shell from the resultant model. The molten or softened thermoplastic composition of the invention is transferred into the vacuum formed shell. The vacuum formed shell containing the thermoplastic composition is then placed directly on the prepared area in the patient's mouth to form the prosthesis.

Yet another type of direct method of fabrication is the free-hand technique. This technique involves syringing or placing the softened thermoplastic composition of the invention onto the practitioner's hand (preferably gloved and lubricated), so that it can be manipulated into a desired preliminary shape and conveniently transferred to the mouth of the patient and applied to the prepared dental area. It has been found that applying the softened thermoplastic composition to the thumb and forefinger of the practitioner's gloved and lubricated hand provides particularly convenient and rapid delivery of the correct amount and approximate shape of the thermoplastic composition.

Alternatively, using the free-hand technique of the direct method of fabrication, the thermoplastic composition may be placed directly onto the prepared dental area in the patient's mouth. The thermoplastic composition is then shaped over the prepared area to fully cover the area.

After application of the material and shaping in the mouth using a free-hand technique, the patient is directed to bring the teeth into occlusion. The provisional prosthesis formed from the thermoplastic composition is allowed to cool or is cooled. The provisional prosthesis is removed from the patient's mouth and excess material is removed from the gingival area by use of a dental instrument such as a crown scissors.

The indirect method of making a provisional prosthetic device is characterized by fabrication of the prosthetic device outside of the patient's mouth. This method involves taking an impression of a dental area both before and after preparation of the area for restorative procedures. Using the single model technique, a positive model is made from the impression of the prepared area using suitable material such as die stone. The molten or softened thermoplastic molding composition of the invention is placed into the impression of the unprepared area at the prepared site. The impression containing the thermoplastic composition is then placed onto the model of the prepared dental area to form the prosthesis.

Alternatively, a dual model technique of the indirect method may be utilized to make a provisional prosthetic device. This technique involves taking an impression of a dental area both before and after preparation of the area for restorative procedures. Models of both the unprepared and the prepared areas are made from their respective impressions using a suitable material such as die stone. A vacuum formed shell is made from the model of the unprepared area. The molten or softened thermoplastic molding composition of the invention is placed into the vacuum formed shell. The vacuum formed shell containing the thermoplastic composition is then placed onto the model of the prepared dental area to form the prosthesis.

With the exception of the free-hand technique, both the direct and the indirect methods of fabrication involve the taking of one or more impressions. The impression may be taken using any suitable elastomeric impression material, such as an alginate, hydrocolloid, polyvinylsiloxane, polyether, polysulfide or condensation silicone. Conventionally, impressioning is facilitated using a rigid plastic, custom acrylic or metal arch-shaped tray typically coated with tray adhesive.

Suitable thermoplastic molding compositions for provisional restorations and crown liners are any thermoplastic materials that are solid at 38° C. Preferably the thermoplastic molding composition comprises a free-radically polymerizable resin. The free-radically polymerizable moiety may be present as a functional portion of the thermoplastic material, more preferably as a separate ingredient in the composition. Most preferably, the thermoplastic molding composition is a blend of a thermoplastic material and a free-radically polymerizable resin. For fabrication using any direct method, the thermoplastic molding composition must not only be solid at 38° C., but must also have a melting or softening point that comfortably can be withstood by oral tissues.

For ease of use with either the direct or the indirect method of fabrication, the thermoplastic composition of the invention is heated to its molten or softened temperature by any heating technique well known in the heating art. Preferably the thermoplastic composition is pre-loaded in an opaque syringe and heated in a low temperature heating unit to a molten or softened temperature suitable for use in the mouth. One such heating assembly is described in co-pending co-assigned U.S. patent application Ser. No.

07/944,966 filed on Sep. 15, 1992, the disclosure of which is incorporated herein by reference.

Regardless of the fabrication method employed, the resultant thermoplastic composition of the provisional prosthetic device or liner is allowed to cool so that it solidifies. If the thermoplastic composition comprises free radically polymerizable functionality, the composition is polymerized by exposure to light from a light source such as a dental curing light. When the provisional prosthesis is fabricated in a preformed crown shell or strip crown or fabricated in the mouth using the free-hand technique, cooling of the thermoplastic composition may be expedited by application of a stream of cold water.

By irradiation from a suitable visible light source, the polymerizable thermoplastic composition of the provisional prosthesis may be partially or fully polymerized at one exposure or a combination of exposures. The composition may be polymerized immediately after fabrication and while still in the patient's mouth, in the impression, on the model or in a prefabricated crown form. Alternatively, the composition may be polymerized after fabrication and before it is trimmed and fit on the dental area or just prior to cementation in place in the mouth.

The thermoplastic molding composition of the invention may also be used as a liner for crowns, especially provisional crowns. The liner fills the space between the prepared tooth and the crown, providing better marginal adaptation. In its cured state, the liner also provides strength to the crown. A crown is lined by partially or totally filling a crown with the thermoplastic composition of the invention, seating the crown on the prepared tooth, and removing the excess liner which is expressed around the gingival margins.

Advantages of the thermoplastic composition of the invention over currently used provisional prosthetic materials and crown liner materials include ease of use with a concurrent time savings, extended working time in the flexible rubbery stage and cure on demand to a final set stage. The composition of the invention also requires no mixing which not only provides a time savings, but also results in minimal air incorporation. Compared with currently available materials, the composition of the invention exhibits more desirable physical properties, undergoing less shrinkage upon polymerization and having a higher rubbery state tear strength. The combination of infinite working time in the flexible rubbery stage and ease of removal from undercuts are unique advantages provided by the thermoplastic composition of the invention. This rubbery material may be removed from the tooth structure for trimming excess material that could cause undesirable locking in place due to the undercuts in the tooth structure. After the temporary restoration is properly trimmed, the final configuration may be set by polymerization. Additionally, the composition of the invention exhibits low odor compared with acrylic materials currently utilized for the fabrication of provisional prosthetic devices. Also the unique properties of the thermoplastic molding composition of the invention allow for resoftening and resultant reshaping of the composition at any stage before final cure.

We believe that no previous commercially available thermoplastic dental molding compositions have provided heat-stable custom shape memory (for brevity, "hot custom memory"). The molding compositions of our invention have hot custom memory, and it is manifested by a semi-permanent or optionally a permanent shape memory that can be deliberately imparted to (or imprinted on) the composition by the user. The memory has heat resistance that overcomes the normal thermoplastic behavior of the composition before the memory is imprinted. Accordingly, the compositions after polymerization and depending on the degree of polymerization can be said to be semi-thermoplastic, or optionally completely converted to a thermoset material, rather than thermoplastic.

In one embodiment, the present invention provides a molding composition useful for dental impressioning and general-purpose modelmaking, comprising a homogeneous blend of a thermoplastic material (for example, polycaprolactone), a free-radically polymerizable resin (for example, a urethane diacrylate oligomer), and a free-radical initiator (for example, a visible-light photoinitiator), the blend being solid at 38° C. and having a melting or softening point that comfortably can be withstood by oral tissues, the composition having semi-thermoplasticity and hot custom memory after the resin is polymerized.

The invention also provides a method for making an impression of dental tissue, comprising the steps of a) enveloping the tissue with a molten or softened molding composition comprising the above mentioned homogeneous blend, and, in either order, b) cooling the composition so that it solidifies and c) causing or permitting the free-radically polymerizable resin to undergo polymerization, whereby a semi-thermoplastic dental tissue impression having hot custom memory is obtained.

The molding compositions of the invention have improved physical properties in both the warm and cool states, especially when a custom-molded shape prepared from a composition of the invention is accidentally or intentionally subjected to elevated temperatures.

A variety of thermoplastic materials can be used in the molding compositions of the invention. Selection of the thermoplastic material should be based in part on the desired end use for the molding composition and the desired properties of the composition in the molten or softened ("warm") and solid ("cool") states. The warm state is characterized by appreciable mass flow of the molding composition under moderate (hand) pressure at some temperature between body temperature (about 38° C.) and, in applications where imparting the shape of the material takes place in the mouth, the maximum temperature that comfortably can be withstood by oral tissues. This maximum temperature is generally thought to be about 75° C., although a maximum of about 65° C. is preferred. The cool state is characterized by sufficient strength and stiffness to permit an acceptably accurate dental impression to be made from the molding composition, and by minimal apparent mass flow of the molding composition under moderate pressure at temperatures below 38° C.

The warm and cool state properties permit the molding composition to be heated to a moderate temperature, manually shaped in the mouth while warm to conform to the shape of hard and soft oral tissue, and cooled within the mouth to form a substantially rigid model.

Representative thermoplastic materials include polyesters and polyurethanes such as those described in U.S. Pat. Nos. 3,382,202, 4,059,715, 4,182,829, 4,327,013, 4,361,538, 4,552,906 and 4,569,342, and copolymers such as those described in U.S. Pat. Nos. 4,659,786, 4,740,245 and 4,768,951. The thermoplastic material preferably is a homopolymer or copolymer of epsilon-caprolactone. The polycaprolactone optionally can contain property-modifying or cross-linkable functional groups (for example hydroxyl, acrylate, methacrylate, epoxy, isocyanato or vinyl groups) if desired.

Preferred polycaprolactones have the formula:

I.

where $R^1$ is an aromatic or a straight chain or branched aliphatic backbone, which can optionally contain one or more non-interfering substituents such as hydroxyl or amine groups, w is 1 if $R^1$ is hydrogen, and w otherwise has an average value of about 1 to about 4, M is oxygen or —$NR^2$— where $R^2$ is hydrogen or a non-interfering aromatic or aliphatic group, and the product of w times x is greater than about 35.

Blends of polycaprolactones can also be employed. Suitable polycaprolactone blends are described in U.S Pat. No. 5,066,231, the disclosure of which is incorporated in this specification by reference.

Preferred commercially available polycaprolactone polymers include "TONE P-700" and "TONE P-767" (40,000 molecular weight) and "TONE P-300" (10,000 molecular weight) polycaprolactone from Union Carbide Corp., and the "CAPA" polycaprolactones "630" (30,000 molecular weight), "640" (40,000 molecular weight), "650" (50,000 molecular weight), and "656" (56,000 molecular weight) from Interox.

The free-radically polymerizable resin contains at least one ethylenically unsaturated monomer, oligomer, or polymer capable of undergoing addition polymerization. Suitable monomers include mono-, di- or polyfunctional acrylates and methacrylates such as methyl acrylate, methyl methacrylate, ethyl acrylate, isopropyl methacrylate, n-hexyl acrylate, styryl acrylate, allyl acrylate, glycerol diacrylate, glycerol triacrylate, ethyleneglycol diacrylate, diethyleneglycol diacrylate, triethyleneglycol dimethacrylate, 1,3-propanediol diacrylate, 1,3-propanediol dimethacrylate, trimethylolpropane triacrylate, 1,3,3-butanetriol trimethacrylate, 1,4-cyclohexanediol diacrylate, pentaerythritol triacrylate, pentaerythritol tetraacrylate, pentaerythritol tetramethacrylate, sorbitol hexacrylate, bis[1-(2-acryloxy)]-p-ethoxyphenyldimethylmethane, bis[1-(3-acryloxy-2-hydroxy)]-p-propoxyphenyldimethylmethane, tris-hydroxyethylisocyanurate triacrylate, beta-methacrylaminoethyl methacrylate, and mixtures thereof. Other suitable monomers include unsaturated amides such as methylene bis-acrylamide, methylene bis-methacrylamide, 1,6-hexamethylene bis-acrylamide and diethylenetriamine tris-acrylamide. Suitable oligomeric or polymeric resins include 200 to 500 molecular weight polyalkylene glycols, acrylated or methacrylated oligomers such as those of U.S. Pat. No. 4,642,126, acrylated urethanes such as "SARTOMER" 9503, 9504 and 9505 (Sartomer Corp.), "INTEREZ" CMD 8803, 8804 and 8805 (Radcure Specialties, Inc.), and "PHOTOMER" 6060, 6110 and 6160 (Henkel Corp.), as well as acrylated polyester oligomers such as "EBERCRYL" 830 (Radcure Specialties, Inc.). Mixtures of free-radically polymerizable monomers, oligomers or polymers can be used if desired.

The free-radically polymerizable resin can if desired be cured using a conventional chemical initiator system, such as a combination of a peroxide and an amine. However, chemical cure initiator systems typically require at least partial ingredient separation before use. The resin is preferably cured using a photoinitiator, optionally combined with a suitable photosensitizer or accelerator. The photoinitiator should be capable of generating free radicals for addition polymerization at some wavelength between 200 and 800 nm. Suitable photoinitiators include alpha-diketones, monoketals of alpha-diketones or ketoaldehydes, acyloins and their corresponding ethers, chromophore-substituted halomethyl-s-triazines, chromophore-substituted halomethyl-oxadiazoles, aryliodonium salts, and other commercially available ultraviolet ("UV") and visible light photoinitiators. Preferred photoinitiator systems include a mono or diketone photoinitiator together with a suitable donor compound or accelerator, such as the systems described in U.S. Pat. Nos. 3,427,161, 3,756,827, 3,759,807, 4,071,424, 4,828,583, U.K. Pat. Specification No. 1,304,112, European Published Pat. Appl. No. 150,952 and Chem. Abs. 95:225704U.

The molding compositions of the invention can contain a wide variety of adjuvants depending upon the desired end use. Suitable adjuvants include solvents, diluents, plasticizers, pigments, dyes, inorganic or organic fibrous or particulate reinforcing or extending fillers, thixotropic agents, indicators, inhibitors, stabilizers, UV absorbers, medicaments (e.g., leachable fluorides), biocides and the like. For custom tray applications, the molding composition preferably contains one or more fillers that limit the composition's 60° C. relaxation stress at equilibrium, as described in European Patent Application No. 516,716.

The types and amounts of ingredients in the molding compositions of the invention usually will be empirically selected. The thermoplastic material and free-radically polymerizable resin preferably are present in "major proportion" and "minor proportion", respectively. By this we mean that the composition preferably contains a higher weight percent of thermoplastic material than of polymerizable resin.

The composition should remain substantially homogeneous (that is, it should not undergo macroscopic phase separation or filler sedimentation). Subject to the effects of any imprinted hot custom memory, the composition preferably should retain its desired physical properties even if repeatedly cycled between the warm and cool states. Thus the selection of ingredients can be guided in part by the desire to preserve homogeneity and thermal reversibility. Also, the amount of polymerizable resin and initiator should be sufficient to provide the desired degree of hot custom memory. Lower amounts of resin tend to increase susceptibility to creep after the custom memory has been imparted to the composition. Higher resin amounts tend to decrease elasticity and increase thermoset characteristics.

As a further guide, the preferred amounts of thermoplastic material, polymerizable resin, initiator and filler for dental impressioning are as follows:

| Ingredient | Preferred Weight % |
|---|---|
| Thermoplastic material | up to 90 |
| Polymerizable resin | up to 50 |
| Initiator | up to 10 |
| Filler | 0–70 |

The ingredients in the molding composition can be blended by hand or by mechanical mixing. The ingredients preferably are warmed sufficiently to melt the thermoplastic material, but if desired can be mixed at lower temperatures. Any suitable mixing device can be used, including kettles equipped with a mechanical stirrer, extruders, rubber mills, and the like.

The molding composition can be put up in a variety of forms including preformed sheets, arch-shaped trays, ropes, buttons, woven or non-woven webs and the like. The composition can be shaped in a variety of ways including extrusion, injection molding and web processing using a coating knife or rollers. The composition can be sold unwrapped, loosely wrapped in a package, or packaged in tubes, syringes, flexible outer plastic skins, plastic or metal trays and the like. The composition can be extruded or cast in mono-, bi-, or poly-layers (for example, aplanar layers or layers arranged in core-shell fashion) in which each layer has a selected melting temperature, viscosity, modulus, stickiness or other desired physical properties.

The molding composition can be converted from the cool state to the warm state by using a variety of energy sources. The composition can be immersed in a heated bath containing a suitable inert liquid (for example, water or a fluorochemical fluid) that will not dissolve or swell the composition in either its cool or warm states. The composition can also be softened using heat sources such as a hot air gun, hot plate, conventional oven, infrared heater or microwave oven. The composition can be encased in a plastic pouch, syringe or other container which is in turn heated (e.g. electrically), or subjected to one or more of the above-mentioned heating methods.

Transforming the molding composition from a warm state to a cool state requires loss of thermal energy and can be carried out using a variety of cooling techniques. Cooling can take place under ambient conditions in the presence of air only. Cooling can be expedited using forced air, cold water, ice, or heat sinks such as chilled "cold packs" or flexible pouches containing low boiling inert liquids. Of particular interest for both dental and orthopedic applications are chilled cold packs in flexible pouches that have been preshaped to match the contours of the model being cooled. For example, flexible pouches containing a chilled coolant can be fabricated in the shape of a full arch or quadrant and placed intraorally in contact with the warm molding composition. Analogously, a large coolant-filled blanket can be draped around an orthopedic casting or splint material prepared from a molding composition of the invention.

Hot custom memory is imparted to the molding composition by allowing or causing the free-radically polymerizable resin and initiator to harden (for example, by exposing a composition containing a photoinitiator to a suitable light source). Polymerization can take place before or after the warmed, softened model is allowed to cool, although carrying out polymerization after cooling will tend to lengthen polymerization times. After polymerization, impression material made from these compositions preferably retain sufficient elasticity to permit the material to be removed from undercut surfaces such as the undercuts typically found in the oral cavity.

The polymerized, cooled model will exhibit hot custom memory. Accordingly, it will be more resistant to heat and handling stresses than models made from the thermoplastic material alone. If the model is accidentally distorted, it can be returned to its custom shape by reheating it in a relaxed condition. For example, the model can be immersed in a hot water bath and removed for cooling after the custom shape has reappeared. While still in the warm state, it may remain pliable, and accordingly will exhibit semi-thermoplasticity. This permits the custom shape to be adjusted if desired.

A simplified dental impression system can be prepared from the molding composition. Traditional impressioning systems employ one or more low viscosity, flowable elastomeric materials such as an alginate, hydrocolloid, polyvinylsiloxane, polyether, or polysulfide contained in a fairly rigid adhesive-coated plastic or metal arch-shaped tray. The elastomeric material often is applied both to the dental tissue to be modeled and to the tray. The elastomeric material and surrounding tray are subsequently pressed against the dental tissue, and left in place until the elastomeric material has hardened. This traditional process involves several materials and steps, material waste and fairly lengthy set times.

The present invention permits impressioning using a monolayer or a bilayer thermoplastic molding composition. The monolayer model, or at least one layer of the bilayer model, is made from a molding composition of the invention. In a preferred embodiment, a flat sheet or a preformed arch-shaped tray is made from two coextruded thermoplastic layers. The physical properties of each layer emulate in part the properties of a conventional rigid tray and the elastomeric material respectively. At a suitable elevated temperature the "tray" layer becomes a conformable, non-sticky melt (thereby permitting the warm tray layer to be hand-shaped into a custom tray configuration) and the "elastomer" layer exhibits good flow and low viscosity (thereby permitting the warm elastomer layer to flow around tooth structure and provide an accurate model). The warm bilayer construction provides easy placement, accurate impressioning, and efficient use of materials. Cooling can take place rapidly, and in less time than is required to harden a conventional impression. Once cooled, the tray layer exhibits sufficient rigidity to discourage distortion of the impression during removal from the mouth or during subsequent handling. If the tray layer is made from a molding composition of the invention and is polymerized after the desired custom shape has been attained, then the hot custom memory properties of the tray layer discourage creep and distortion. The elastomer layer provides stable, accurate modeling of hard and soft dental tissue. If the elastomer layer is made from a molding composition of the invention, then the hot custom memory properties of the elastomer layer aid in making accurate casts using heated gypsum stone substitutes such as hot-melt thermoplastics. In either embodiment, the model can be shipped through the mail and exposed to elevated temperatures with reduced risk that the model will melt or otherwise become permanently distorted.

If desired, a custom impression tray can be formed from a molding composition of the invention and filled with a conventional elastomeric impression material (for example, a silicone elastomer). By shaping the tray in the mouth before (or if desired, after) it is filled with elastomer, the tray volume and required amount of elastomer will be minimized.

The molding compositions of the invention have many other uses. For example, they can be used to prepare crowns, bridges, dentures, splints and pontics. They can also be used to prepare shapeable orthopedic casts and splints. They can be used in modelmaking, for example in tool and die-making. They will find general use in applications requiring rapid, accurate shaped object formation.

The following examples are offered to aid in understanding the invention and are not to be construed as limiting its scope. Unless otherwise indicated, all parts and percentages are by weight. Irradiation of all provisional restorations was carried out for the designated amount of time while moving the light over all exposed surfaces of the restoration. All final provisional restorations were finished, polished and adjusted with appropriate burrs and disks as required.

EXAMPLE 1

70 Parts "TONE P-767" (40,000 molecular weight) polycaprolactone and 30 parts "SR-9503" urethane diacrylate oligomer were placed in an open vessel and heated in an oven at 80° C. until both components were fluid. The vessel was transferred to an 80° C. water bath and the mixture stirred until homogeneous. While working under a safelight, 0.50 parts camphorquinone ("CPQ") and 0.50 parts p-ethyldimethylaminobenzoate ("EDMAB") were dissolved in the mixture with stirring. The resultant blend was poured onto polyester sheeting atop a horizontal platform. A second polyester sheet was placed atop the molten mass. A roller was used to form the blend into sheets of approximately 204 mm thickness. The sheets were transparent while warm and became opaque when cooled under a stream of cold water.

Using a similar procedure a control composition (containing 100% polycaprolactone) and fifteen additional polycaprolactone/acrylate blends were prepared. Set out in TABLE I are the types and amounts of polycaprolactone ("PCL") and acrylate in each composition, and several physical properties for each composition. Warm state viscosity was measured at 65° C. using a rheometric dynamic analyzer (Rheometrics, Inc.) operated at 20% maximum strain and 1 radian/second strain rate.

Cool state storage modulus was measured at 30° C. on the rheometric dynamic analyzer, operated at 1.4% maximum strain and a 10 radian/second strain rate, on samples subjected to several curing conditions. The samples were 1) not irradiated 2) irradiated under "cold" conditions while the sample was at 25° C. in a custom-molded configuration, using a "VISILUX 2" dental curing lamp (3M) operated for two minutes, or 3) irradiated under "hot" conditions while the sample was at about 50°–55° C. in a custom-molded configuration, using the same lamp and time as in 2). These three conditions are identified as "NIR", "IR Cold", and "IR Hot" in the tables that follow. Dimensional stability was evaluated using a modified version of American Dental Association (ADA) Test Specification No. 19 (*J.A.D.A.*, 94., 733 (1977)). Each molding composition was heated to 80° C. until molten and poured onto the ruled die prescribed in the Test Specification. A transparent rigid plate was placed atop the molten composition, and secured to the ruled die with a clamp. Selected samples of the composition were left unirradiated or irradiated while hot. The molten composition was allowed to cool for 5 minutes at room temperature. Selected molding composition samples were irradiated while cold. The clamp and solidified molding composition were removed from the die. The resulting model was stored at 23°±1° C. and 50±5% relative humidity for 24 hours. Dimensional stability was determined by comparing the distances between the ruled lines on the model and on the ruled die using an optical comparator.

TABLE I

| Run No. | PCL Type | PCL Parts | Acrylate Type | Acrylate Parts | Viscosity 65° C., kilopoise | Modulus, 30° C. dyne/cm$^2$ × 10$^8$ | | | Dimensional stability, % shrinkage | | |
|---|---|---|---|---|---|---|---|---|---|---|---|
| | | | | | | NIR[2] | IR Cold[3] | IR Hot[4] | NIR | IR Cold | IR Hot |
| 1 | P-767[1] | 100 | None | 0 | 85.0 | 11.7 | NM[5] | NM | 0.70 | NM | NM |
| 2 | P-767[1] | 70 | SR-9503[6] | 30 | 52.7 | 4.2 | 7.8 | 5.5 | 0.47 | 0.49 | 0.55 |
| 3 | P-767[1] | 55 | SR-9503[6] | 45 | 9.2 | 0.9 | 5.2 | 5.6 | NV[7] | 0.40 | 0.45 |
| 4 | P-767[1] | 70 | SR-9504[8] | 30 | 35.1 | 5.9 | 4.9 | 4.5 | 0.54 | 0.58 | 0.53 |
| 5 | P-767[1] | 55 | SR9504[8] | 45 | 12.8 | 3.3 | 4.3 | 8.3 | 0.57 | 0.57 | 0.51 |
| 6 | P-767[1] | 70 | SR-9505[9] | 30 | 35.0 | 6.1 | 11.0 | 9.2 | 0.58 | 0.56 | 0.49 |
| 7 | P-767[1] | 55 | SR-9505[9] | 45 | 20.4 | 3.8 | 10.0 | 13.9 | NV | 0.28 | 0.41 |
| 8 | P-767[1] | 70 | CMD-8803[10] | 30 | 32.8 | 0.01 | 6.2 | 9.7 | 0.51 | 0.35 | 0.46 |
| 9 | P-767[1] | 55 | CMD-8803[10] | 45 | 6.2 | 0.8 | 6.4 | 4.8 | NM | 0.34 | 0.41 |
| 10 | P-767[1] | 70 | CMD-8805[11] | 30 | 23.6 | 9.1 | 24.1 | 16.9 | 0.57 | 0.69 | 0.70 |
| 11 | P-767[1] | 55 | CMD-8805[11] | 45 | 11.3 | 3.8 | 0.2 | 31.3 | 0.38 | 0.66 | 0.73 |
| 12 | P-767[1] | 70 | 230[12] | 30 | 11.4 | 7.6 | 8.2 | 7.3 | NV | 0.41 | 0.50 |
| 13 | P-767[1] | 55 | 230[12] | 45 | 15.4 | 5.6 | 5.7 | 6.7 | NV | 0.25 | 0.44 |
| 14 | P-767[1] | 70 | 4287[13] | 30 | 12.7 | 6.1 | 9.2 | 8.6 | 0.43 | 0.59 | 0.58 |
| 15 | P-767[1] | 55 | 4287[13] | 45 | 49 | 4.1 | 6.3 | 4.5 | 0.39 | 0.53 | 0.49 |
| 16 | P-767[1] | 70 | 830[14] | 30 | 0.1 | 0.03 | 19.0 | 11.6 | 0.32 | 0.83 | 0.63 |
| 17 | P-767[1] | 55 | 830[14] | 45 | 0.03 | NM | 12.7 | 5.5 | 0.23 | 1.01 | 1.16 |

[1]"TONE P-767" 40,000 molecular weight polycaprolactone (Union Carbide Corp.).
[2]"NIR" — Not irradiated.
[3]"IR Cold" = Irradiated cold.
[4]"IR Hot" + Irradiated hot.
[5]"NM" = Not measured.
[6]"SR-9503" urethane diacrylate oligomer (Sartomer Corp.).
[7]"NV" = Measurement attempted but not recorded due to poor die reproduction.
[8]"SR9504" urethane diacrylate oligomer (Sartomer Corp.).
[9]"SR-9505" urethane diacrylate oligomer (Sartomer Corp.).
[10]"CMD-8803" urethane diacrylate oligomer (Radcure Specialties, Inc.).
[11]"CMD-8805" urethane diacrylate oligomer (Radcure Specialties, Inc.).
[12]"Ebercryl 230" Urethane acrylate (Radcure Specialties, Inc.).
[13]"Ebercryl 4287" Aromatic urethane acrylate (Radcure Specialties, Inc.).
[14]"Ebercryl 830" polyester hexacrylate (Radcure Specialties, Inc.).

Figure 1:
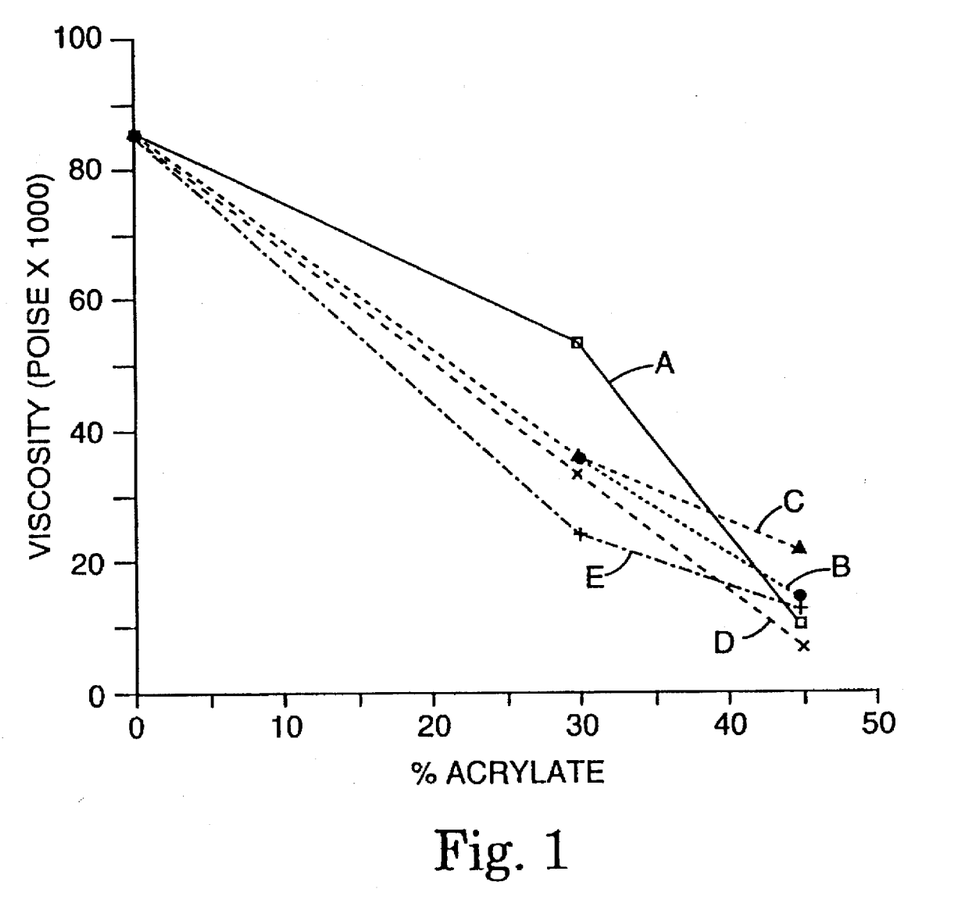
FIG. 1 is a plot of viscosity vs. percent acrylate resin for the compositions of Runs 1–11 of EXAMPLE 1.

The above data illustrates the extent to which a reduction in warm state viscosity, an increase in cool state modulus, and a reduction in shrinkage can be attained by blending polycaprolactone with free-radically polymerizable resin And photoinitiator, and irradiating the blend under hot or cold conditions. The data is further illustrated in FIGS. 1 and 2. FIG. 1 shows an unsmoothed plot of viscosity at 65° C. vs. percent polymerizable resin for Runs 1–11 of TABLE I. Curves A through E connect the data points for blends containing the polymerizable resins "SR-9503", "SR-9504", "SR-9505", "CMD-8803" and "CMD-8805", respectively.

Figure 2:
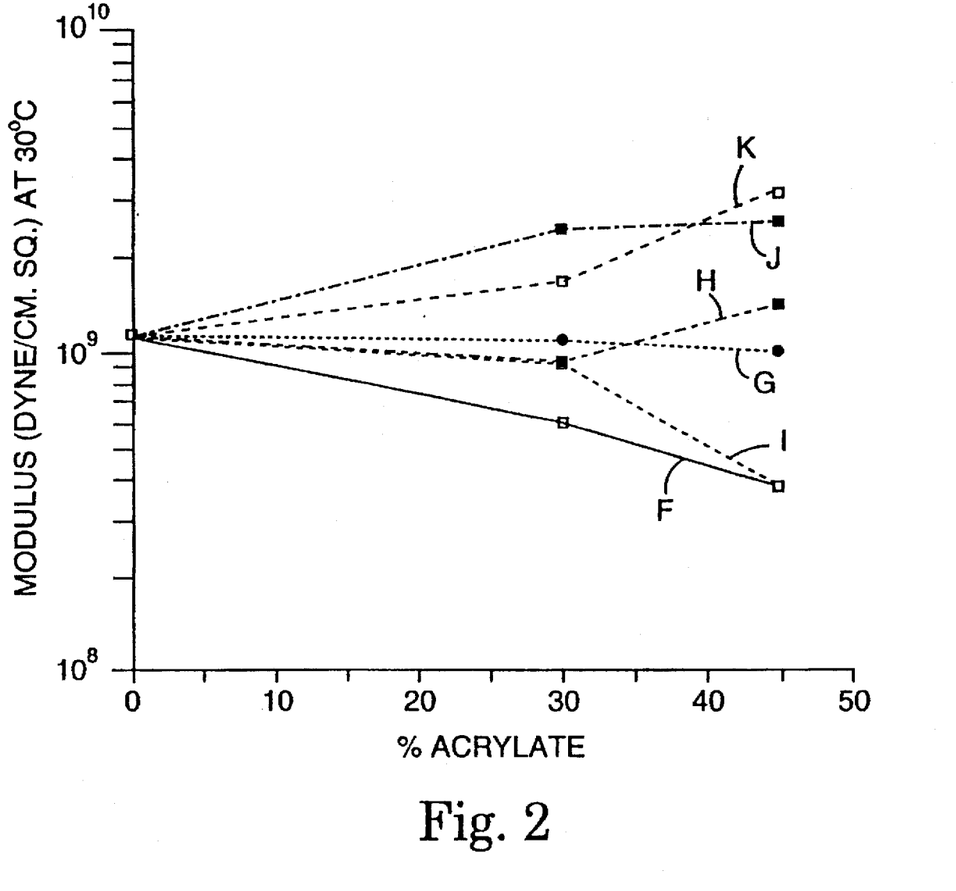
FIG. 2 is a plot of storage modulus vs. percent acrylate resin for the compositions of Runs 1, 6, 7, 10 and 11 of EXAMPLE 1.

FIG. 2 shows an unsmoothed plot of storage modulus at 30° C. vs. percent polymerizable resin for the compositions of Runs 1, 6, 7, 10 and 11. Curves F, G, and H are for compositions containing "SR-9505" polymerizable resin and polymerizable resin ("Resin") in each composition, the type and amount of filler in each composition, and the modulus for compositions that were not irradiated ("NIR") or irradiated while cold ("IR Cold").

TABLE II

| | Ingredients | | | | Modulus, 30° C., dynes/cm² × 10⁸ | |
|---|---|---|---|---|---|---|
| | PCL | Resin | Filler | | | |
| Run No. | Amount | Amount | Type | Amount | NIR | IR cold |
| 1 | 74.0 | 24.5 | — | — | 3.2 | 8.1 |
| 2 | 54.0 | 24.5 | "IMSIL"¹ | 20 | 5.1 | 7.1 |
| 3 | 39.0 | 19.5 | "IMSIL"¹ | 40 | NM² | 2.8 |
| 4 | 54.0 | 24.5 | "VICRON"³ | 20 | 1.5 | 8.6 |
| 5 | 39.0 | 19.5 | "VICRON"³ | 40 | NM | 9.1 |
| 6 | 54.0 | 24.5 | "DUROSIL"⁴ | 20 | 7.0 | 8.1 |
| 7 | 54.0 | 24.5 | "OX-50"⁵ | 20 | 3.9 | 9.4 |
| 8 | 54.0 | 24.5 | Treated "OX-50"⁶ | 20 | 3.9 | 9.4 |
| 9 | 54.0 | 24.5 | Quartz⁷ | 20 | 8.4 | 6.9 |

¹"IMSIL A-25" Quartz filler (Illinois Minerals).
²NM — not measured
³"VICRON" calcium carbonate (Pfizer Corp.).
⁴"Durosil" silica (North American Silica Co.).
⁵"OX-50" pyrogenic silica (Degussa).
⁶"OX-50" pyrogenic silica treated with gamma-methacryloxypropyl trimethoxysilane.
⁷quartz treated with gamma-methacryloxypropyl trimethoxysilane.

(Runs 6 and 7) in the unirradiated, irradiated cold and irradiated hot conditions, respectively. Curves I, J and K are for compositions containing "CMD-8805" polymerizable resin (Runs 10 and 11) in the unirradiated, irradiated cold and irradiated hot conditions, respectively. As shown by the curves, the irradiated compositions exhibited improved modulus compared to unirradiated compositions.

Figure 3:
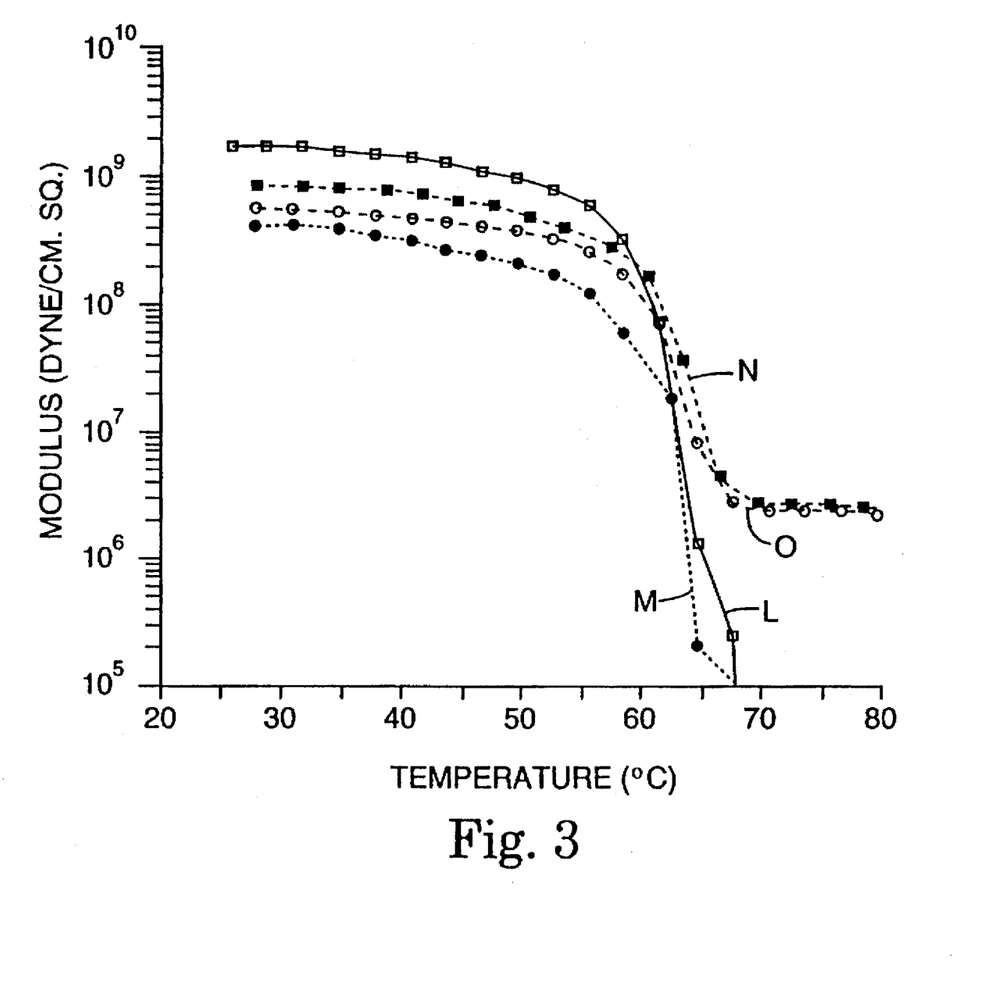
FIG. 3 is a plot of storage modulus for the compositions of Runs 1 and 2 of EXAMPLE 1, showing the effect of imparting hot custom memory to the composition of Run 2 under various conditions.

Referring now to FIG. 3, an unsmoothed plot of storage modulus vs. temperature is shown for Run 1 (curve L) and Run 2 (curves M, N and O) of TABLE I. The measurements were made using a rheometric dynamic analyzer operated at 1.4% maximum strain and a 10 radians/second strain rate. Curve L is a control, and illustrates the substantial decrease in modulus that occurs when the temperature of the molding composition exceeds its melting or softening temperature. Curves M through O illustrate the modulus of a polycaprolactone/polymerizable resin blend in the unirradiated, irradiated cold and irradiated hot conditions, respectively. As shown by curves N and O, modulus remains high and is relatively unaffected by temperature. These compositions thus have significantly improved heat resistance.

EXAMPLE 2

20 Parts "IMSIL A-25" ground quartz filler (Illinois Minerals) were added with stirring to an open vessel containing 24.5 parts "CMD-8805" urethane acrylate oligomer, 0.5 parts CPQ and 1.0 parts EDMAB. The mixture was stirred at 80° C. until homogeneous. 54 Parts "TONE P-767" polycaprolactone were added to the vessel, and the mixture was heated with stirring at 80° C. until molten.

Using a similar procedure, a control composition containing no filler and eight additional compositions containing various types and amounts of fillers were prepared. Set out in TABLE II are the amounts of polycaprolactone ("PCU")

EXAMPLE 3

An aliphatic segmented thermoplastic polyester was prepared by measuring out the ingredients set out below in TABLE III:

TABLE III

| Ingredient | Parts |
|---|---|
| Poly(tetramethylene ether) diol¹ | 49.53 |
| Adipic acid | 29.21 |
| 1,6-hexanediol | 21.26 |
| Antioxidant² | 0.10 |
| Antimony oxide | 0.10 |

¹"POLYMEG 2000" (Quaker Oats Chemical).
²"IRGANOX 1010" (Ciba Geigy Corp.).

The "POLYMEG 2000" diol and 1,6-hexanediol were transferred to a three neck flask fitted with a mechanical stirrer, condenser, "Dean-Stark" trap, heating mantle, thermometer and nitrogen inlet. The diols were stirred at moderate speed under a nitrogen purge for 5–10 minutes while heating to a temperature of 100° C. Adipic acid was slowly added and the mixture heated to a temperature of about 140°–150° C. Water began collecting in the trap. The reaction was continued until at least 80% complete on the basis of water volume collected. The reaction mixture was cooled to 150° C. and the trap removed. The antioxidant and antimony oxide were then added to the flask. The flask was purged with nitrogen for 5 minutes. Following the purge, the flask was attached to a vacuum line and the pressure reduced while maintaining a reaction temperature of 150° C. After 30 to 60 minutes a vacuum of <0.1 mm Hg was attained and the reaction temperature increased to 230° C. The reaction was continued until the acid number had decreased to less than <1 mg KOH gm sample. The resulting semi-crystalline thermoplastic composition contained about 53% amorphous segment content and exhibited rubbery, elastomeric properties in the solid state.

A blend of this segmented polyester and a free-radically polymerizable acrylate resin ("CMD-8803", Interez) was prepared by transferring the ingredients set out below in TABLE IV to a glass vessel heated to 80° C.:

TABLE IV

| Ingredient | Parts |
| --- | --- |
| Segmented polyester | 80.0 |
| Urethane acrylate | 20.0 |
| CPQ | 0.25 |
| EDMAB | 0.50 |

The ingredients were heated until molten and mixed thoroughly with a spatula until homogeneous. The resultant blend was cast into a sheet and cooled, yielding a thermoplastic elastomer.

The neat segmented polyester and the segmented polyester/acrylate blend were evaluated by measuring viscosity, modulus, and shrinkage as described above. In addition, compression set was evaluated using a modified version of ADA Test Specification No. 19.. Each composition was heated to 80° C. until molten and transferred to the standard compression set cylindrical mold prescribed in the Test Specification. The mold endplates were clamped into place and the mold and its contents cooled in a 22° C. water bath for 5 minutes. The resulting solidified model was removed from the mold. Each model was axially compressed 1.0 mm for 30 seconds using a metered screw clamp. The clamp was released and a measurement of permanent deformation recorded one minute later. The percentage change in cylinder height was calculated to determine compression set.

Strain-in-compression was evaluated using a modified version of ADA Test Specification No. 19. Cylindrical models were prepared according to the compression set test described above. The cylinder height was measured, a 1.125 kg mass was placed atop the cylinder, and a second height measurement was recorded thirty seconds later. The percentage change in cylinder height was calculated to determine strain-in-compression.

The results for each composition are set out in TABLE V:

TABLE V

| Run No. | Polyester/ acrylate ratio | Viscosity, 65° C., kilopoise | Modulus, 30° C., dyne/cm$^2$ × 10$^8$ | | Dimensional stability, % shrinkage | | Compression set, % | Strain-in-compression, % |
| --- | --- | --- | --- | --- | --- | --- | --- | --- |
| | | | NIR$^1$ | IR Hot$^2$ | NIR | IR Hot | | |
| 1 | 100/0 | 2.7 | 0.5 | NM$^3$ | 0.25 | NM | 0.96 | 0.63 |
| 2 | 80/20 | 2.2 | 0.6 | 0.8 | 0.23 | 0.12 | 0.84 | 1.78 |

$^1$"NIR" = Not irradiated.
$^2$"IR Hot" + Irradiated hot.
$^3$"NM" = Not measured.

EXAMPLE 4

Three compression set cylinders were prepared from the polycaprolactone/acrylate blend of Run 7 of TABLE I, and evaluated for compression set as in EXAMPLE 3. However, one cylinder was irradiated with a "VISILUX 2" curing light through the clamped clear plastic endplates while the composition was in the molten state. The second cylinder was irradiated after the composition had been cooled and removed from the cylindrical mold. The third cylinder was not irradiated. The three cylinders were each removed from the mold and evaluated for hot custom memory in the following manner. Each cylinder was independently placed in an 80° C. water bath for 5 minutes. The unirradiated cylinder melted and failed to maintain its cylindrical shape. Both of the irradiated cylinders exhibited only softening to an elastomeric condition. Each of the irradiated cylinders was measured lengthwise, axially compressed 2.4 mm and cooled while compressed so that a semi-permanent 2.4 mm lengthwise distortion was imparted. The cylinders were then reheated in an 80° C. water bath for 5 minutes, allowed to cool until solid and then measured lengthwise for comparison to the original cylinder length prior to compression. The cylinder irradiated in the solid state exhibited 99.86% recovery, and the cylinder irradiated in the molten state exhibited 99.75% recovery. These irradiated samples thus exhibited excellent hot custom memory, whereas the unirradiated cylinder exhibited no memory.

EXAMPLE 5

Inlay accuracy was evaluated by heating the molding compositions of Runs 8–11 of TABLE I and Runs 1 and 2 of TABLE V to 65° C., and using the resulting molten compositions to make an impression of a Class II MOD preparation on the lower left first molar of a "TYPODONT" model (Columbia Dentoform Corp.). The molten compositions were applied evenly to the second premolar, the prepared first molar and the second molar, and pressed into place using finger pressure while in the transparent, molten state. Each composition was cooled for 60 seconds using a stream of cold water and then removed from the TYPODONT model yielding a completed opaque impression. A standard gypsum "stone" model was poured in each impression. The hardened stone model was easily removed from the impression by slightly warming the impression to about 60° C. in a water bath. An inlay was fabricated on each stone model in the following manner. A thin film of room-temperature vulcanizing silicone ("IMPRINT", 3M) was applied to the MOD preparation on the stone model and allowed to cure. Light curable restorative material ("SILUX PLUS", 3M) was tamped into the MOD preparation and shaped and carved to provide proper fit and anatomy. The restorative material was irradiated with a VISILUX 2 curing lamp for 60 seconds. The resulting photohardened inlays were removed from the stone model and evaluated for overall fit on the original TYPODONT model preparation. Inlays were rated by two evaluators as providing excellent ("++"), acceptable "+"), or unacceptable ("−") fit. The results are set out in TABLE VI:

TABLE VI

| Table No. | Run No. | Thermo-plastic/ acrylate ratio | Inlay fit | | | |
|---|---|---|---|---|---|---|
| | | | NIR[1] | IR Hot[2] | IR Cold-IO[3] | IR Cold-EO[4] |
| I | 8 | 70/30 | ++ | ++ | +/++ | +/− |
| I | 9 | 55/45 | − | − | ++ | ++ |
| I | 10 | 70/30 | − | ++ | − | − |
| I | 11 | 55/45 | − | ++ | ++ | ++ |
| V | 1 | 100/0 | ++ | NM[5] | NM | NM |
| V | 2 | 80/20 | ++ | ++ | NM | NM |

[1]"NIR: = Not irradiated.
[2]"IR Hot" = Irradiated hot.
[3]"IR Cold-IO" = Irradiated cold "intraorally" (white on model).
[4]"IR Cold-EO" = Irradiated cold "extraorally" (after removal from model).
[5]"NM" = Not measured.

The above data illustrates a variety of techniques for preparing inlays from compositions of the invention. For some compositions, excellent inlay fit was obtained even though irradiation was not carried out until after the composition had been cooled to a solid state and removed from the model.

EXAMPLE 6

A filled thermoplastic custom tray composition was prepared by combining 22.5 parts "TONE P-767" polycaprolactone, 7.5 parts "SR-9505" urethane diacrylate, 1.2 parts "EBERCRYL 830" polyester hexacrylate, 45 parts "VICRON" calcium carbonate (Pfizer Corp.), 10 parts "SIPERNAT D-11" treated precipitated silica (North American Silica Co.), 5 parts "ULTRASIL VN-SP3" untreated precipitated silica (North American Silica Co.), 4 parts "1156" chopped glass fibers (PPG), and 0.75 parts each CPQ and EDMAB. The ingredients were stirred in a warm vessel at about 100° C. until homogeneous. The resulting mixture was cast atop polyester film into a 2.5 mm thick sheet into which was pressed a web of "SONTARA 8000" nonwoven material (E. I. DuPont de Nemours & Co.). The warm sheet was cut into generally U-shaped pieces using a "cookie cutter" style cutting implement. Each piece was squeezed while still warm between two halves of a silicone mold to form an arch-shaped, nonwoven web-lined customizable tray. The tray could be reheated and shaped while warm to conform to a patient's dentition. When irradiated for two minutes in a "STAR-CURE" curing chamber (Star X-ray, Inc.), a tray with hot custom memory was obtained. The tray can also be photocured by setting it under a conventional dental operatory light, (for example, a "RITTER STAR LIGHT", Sybron Corp.) for about two minutes per side.

EXAMPLE 7

Using the method of EXAMPLE 1, a photosettable thermoplastic composition was prepared by mixing the ingredients set out below in TABLE VII:

TABLE VII

| Ingredient | Parts |
|---|---|
| "TONE P-767" Polycaprolactone | 59.40 |
| "SR-9505" Urethane diacrylate | 39.60 |
| CPQ | 0.50 |
| EDMAB | 0.50 |

The resulting thermoplastic composition is useful as a crown and bridge material. A bridge was prepared in the following manner. The thermoplastic composition was transferred to a syringe and placed in a 70° C. water bath for about 5 minutes. The second molar was removed from a "TYPODONT" model, and the adjacent first and third molars were prepared as abutment teeth. The thermoplastic composition was syringed onto the abutment teeth and into the gap between them. The composition was shaped while warm to form a bridge with appropriate anatomical form. The bridge was then irradiated for 30 seconds with a "VISILUX 2" curing light. The bridge was allowed to cool, removed from the model and irradiated thoroughly for an additional 60 seconds. The bridge could be firmly reseated on the model. It could be adhered intraorally to actual abutment teeth using a standard dental adhesive such as "SCOTCHBOND" Dual Cure adhesive (3M).

EXAMPLE 8

A crown was fabricated from the composition of EXAMPLE 7. The resulting crown was fairly rigid and could be bonded to a prepared tooth using a standard dental adhesive or cement.

EXAMPLE 9

Using the method of EXAMPLE 1, a photosettable thermoplastic custom tray was fabricated from a composition prepared by mixing together the ingredients set out below in TABLE VIII:

TABLE VIII

| Ingredient | Parts |
|---|---|
| "TONE P-767" Polycaprolactone | 27.0 |
| "CMD 8805" Urethane diacrylate | 12.3 |
| CPQ | 0.5 |
| EDMAB | 0.5 |
| "IMSIL A-25" Filler | 10.0 |

The resulting thermoplastic composition was fabricated into a partially formed tray having a half-moon shape and a protruding handle at the midline. The tray (excluding its handle) was suspended in a 70° C. water bath until transparent, then shaped to fit around the full arch of a "TYPODONT" model. The tray was allowed to cool slightly and then removed from the model. The resulting custom tray was uniformly irradiated with a "VISILUX 2" curing light for about 2 minutes, yielding a rigid photoset tray. The tray was placed in an 80° C. oven for 10 minutes. It retained its shape without slumping, thus illustrating the heat resistance imparted by hot custom memory.

"EXPRESS" tray adhesive (3M) was applied to the photoset custom tray with a brush and allowed to dry for about 5 minutes. "IMPRINT" single phase impression material (3M) was syringed onto the model and into the tray. The tray was reseated on the model and the impression material allowed to set for about 5 minutes. Upon removal of the tray from the model the impression material remained firmly adhered to the tray.

EXAMPLE 10

Using the method of EXAMPLE 9, an unirradiated customizable tray was prepared and placed in a ressalable polyethylene bag of dimensions slightly greater than the tray. The bag was immersed in 70° C. water until the full arch portion of the tray was transparent. The bag was removed from the water, and the bag and tray shaped to fit the full arch of a "TYPODONT" model. After cooling, the custom tray was easily removed from the bag. The bag serves as a convenient custom tray enclosure that discourages mess and contamination, and serves as a spacer between the dental tissue and tray. The spacer allows clearance for adequate amounts of impression material when a final impression is formed.

EXAMPLE 11

A dental die stone substitute was prepared by blending the ingredients set out below in TABLE IX at 80° C. until homogeneous.

TABLE IX

| Ingredient | Parts |
| --- | --- |
| "TONE P-300" Polycaprolactone | 39.3 |
| "CMD 8805" Urethane diacrylate | 9.8 |
| CPQ | 0.5 |
| EDMAB | 0.5 |
| "EBERCRYL 830" Polyester Hexacrylate | 0.8 |
| "VICRON" Calcium carbonate | 49.1 |

The resulting low viscocity thermoplastic molding composition was transferred to a syringe and delivered while warm into an inverted silicone elastomer full arch impression of a "TYPODONT" model. The impression was filled to above the gumline. The composition was irradiated on its back (gum) side only for 2 minutes with a "STAR-CURE" curing unit and transferred to a cold water bath for 2 additional minutes. The solidified model was removed from the silicone elastomer, yielding a rigid, highly detailed reproduction of the dentition. The solidified model was irradiated for an additional 2 minutes, yielding a model with excellent hot custom memory.

EXAMPLE 12

Using the method of EXAMPLE 1, a thermoplastic composition was prepared by mixing the ingredients set out below in TABLE X.

TABLE X

| Ingredient | Amount (g) |
| --- | --- |
| Capa 650[1] | 8.56 |
| Capa 640[2] | 8.56 |
| Ebercryl 1830[3] | 27.18 |
| Filler[4] | 54.50 |
| Camphoroquinone | 0.20 |
| Ethyl dimethylaminobenzoate | 0.20 |
| Tinuvin P[5] | 0.11 |
| Sodium Carbonate | 0.636 |

[1]Polycaprolactone, 50,000 molecular weight, Interox.
[2]Polycaprolactone, 40,000 molecular weight, Interox.
[3]Acrylated polyester oligomer, Radcure Specialties, Inc.
[4]Quartz filler treated with about 5.7% gamma-methacryloxpropyl trimethoxysilane (A-174, Union Carbide Corp.).
[5]2-(2'-Hydroxy-5',-methylphenyl)benzotriazole, Ciba-Geigy Corp.

The resultant thermoplastic composition was loaded into an opaque syringe. The syringe was placed in a heating assembly prepared by modifying a 3M™ Attest™ Biological Monitoring System (from 3M). The assembly consisted of a base heater, an anodized aluminum block for heat transfer and a cover. The heating assembly was designed to warm one or two syringes of the thermoplastic composition to approximately 56°–60° C. in about 15–20 minutes.

The softened thermoplastic composition was used to independently prepare a provisional crown and bridge using the direct method of fabrication. An impression of a dental area of a patient was made prior to preparation of the dental area for restorative procedures. Jeltrate™ alginate impression material (from L. D. Caulk/Division of Dentsply International, Inc.) was placed in a plastic arch-shaped tray. The loaded tray was placed in the patient's mouth and left in place on the unprepared area until the impression material had hardened (about 3–4 minutes). The softened thermoplastic composition was syringed into the impression at the site of the prepared area. The impression containing the thermoplastic composition was then placed on the prepared dental area in the patient's mouth to form a prosthesis. This impression tray was maintained in place in the patient's mouth until the thermoplastic composition solidified to a flexible rubbery state (approximately 2 minutes).

The impression tray was removed from the patient's mouth, leaving the prosthesis in place on the prepared area. The prosthesis was removed from the prepared area, trimmed with a crown scissors and reseated in the patient's mouth to check the fit. The prosthesis was removed from the patient's mouth and irradiated with a 3M™ Visilux™ 2 Visible Light Curing Unit (from 3M) for approximately 30 seconds per unit. The resultant prosthesis was cemented in place on the prepared dental area using Temp-Bond NE™ temporary crown and bridge cement (from Kerr/Sybron Manufacturing Company, Inc.).

EXAMPLE 13

A provisional crown and bridge were independently fabricated using the composition of EXAMPLE 12. The prostheses were prepared using the procedure of EXAMPLE 12, except that prior to removal of the prosthesis from the prepared area, the prosthesis was irradiated in the patient's mouth with a Visilux 2 light for approximately 5 seconds per unit. Additionally, before cementation in the mouth, the prosthesis was further irradiated with a Visilux 2 light for about 20–30 seconds per unit.

EXAMPLE 14

A provisional crown and bridge were independently fabricated using the composition of EXAMPLE 12 and utilizing the single model technique of the indirect method of fabrication.

An impression of a dental area was taken both before and after preparation for restorative procedures using 3M™ Imprint™ 2:5 Impression Material (from 3M) in a rigid plastic tray coated with tray adhesive. The trays containing impression material were independently seated in the patient's mouth and left in place on the dental area until the impression material had hardened (about 3–4 minutes).

Die Keen™ die stone (from Modern Materials) was used to make a die stone model from the impression of the prepared area. A thin layer of petroleum jelly was applied with a cotton swab to the area of the impression of the unprepared area which would contain the thermoplastic material. The softened thermoplastic composition was syringed into the impression of the unprepared area at the site of the prepared area. This impression was then placed on the model of the prepared dental area to form a prosthesis. The tray was maintained in place on the model for about 3–4 minutes until the thermoplastic composition solidified. The tray was then removed from the model.

The prosthesis was removed from the impression material by flexing the tray, trimmed and reseated on the model of the prepared area to check the fit. The pro%thesis was irradiated on the model with a Visilux 2 light for approximately 20 seconds per unit. The prosthesis was removed from the model and the unexposed surface of the prosthesis was irradiated with a Visilux 2 light for an additional 10 seconds per unit. The resultant prosthesis was cemented in place on the prepared dental area using Temp-Bond NE temporary cement.

EXAMPLE 15

A provisional crown and bridge were independently fabricated using the composition of EXAMPLE 12 and employing the dual model technique of the indirect method of fabrication.

An impression of a dental area of a patient was taken both before and after preparation for restorative procedures. Models were prepared from the impressions of both the unprepared and prepared areas. The impression material and the die stone material were as detailed in EXAMPLE 12 and EXAMPLE 14 respectively. The stone model of the unprepared area was placed on a Sta-Vac Mini Lab vacuum form apparatus (from Buffalo Dental).

A vacuum formed shell was made from a 12.7 cm square sheet of polyethylene (from Patterson Dental). The polyethylene sheet was placed in a holding framework and heated to a near melt state. When the polyethylene sheet had slumped about 1.27–2.54 cm below the holding framework, the sheet was pulled down over the stone model of the unprepared area. The vacuum pump of the Sta-Vac vacuum form apparatus was activated and a shell was formed over the model. The shell was allowed to cool for about 2 minutes, removed from the model and trimmed to the desired size using a crown scissors.

The softened thermoplastic composition was syringed into the vacuum formed shell to fill about two-thirds of the shell. The vacuum formed shell containing the thermoplastic composition was then placed on the model of the prepared area and maintained in place for approximately 3–4 minutes until the thermoplastic composition solidified.

The shell containing the prosthesis was then removed from the model. The prosthesis was carefully removed from the vacuum formed shell by flexing the shell. The prosthesis was irradiated with a Visilux 2 light as detailed in EXAMPLE 12, checked for fit and cemented in the patients's mouth as described in EXAMPLE 12.

EXAMPLE 16

A provisional crown and bridge were independently fabricated using the composition of EXAMPLE 12 and the fabrication method described in EXAMPLE 15, except that after removal of the prosthesis from the vacuum formed shell, the prosthesis was irradiated with a Visilux 2 light for approximately 5 seconds per unit. Then the prosthesis was trimmed, checked for fit in the patient's mouth, removed from the mouth and irradiated with a Visilux 2 light for an additional 20–30 seconds per unit. The prosthesis was then cemented in place in the patient's mouth as described in EXAMPLE 12.

EXAMPLE 17

A provisional crown and bridge were independently fabricated using the procedure of EXAMPLE 15 with the exception that after the thermoplastic composition in the vacuum formed shell had solidified on the model, the prosthesis was irradiated in the vacuum formed shell on the model with a Visilux 2 light for 30 seconds per unit. The vacuum formed shell containing the prosthesis was then removed from the model, trimmed, reseated on the model to check fit and cemented in place in the patient's mouth using Temp-bond NE temporary cement.

EXAMPLE 18

A provisional crown and bridge were independently fabricated using the procedure of EXAMPLE 15, except that after the thermoplastic composition in the vacuum formed shell had solidified on the model, the prosthesis was irradiated in the vacuum formed shell on the model with a Visilux 2 light for about 20 seconds per unit. Then the shell was removed from the model and the underside of the prosthesis was irradiated with a Visilux 2 light for an additional 10 seconds per unit. The vacuum formed shell was removed from the prosthesis, the prosthesis was trimmed, reseated on the model to check for fit and cemented in place in the patient's mouth using Temp-Bond NE temporary cement.

EXAMPLE 19

Provisional crowns and bridges were independently fabricated using the procedure of EXAMPLE 15, except that a model was made from the impression of only the unprepared area. After the thermoplastic composition was syringed into the vacuum formed shell, the shell containing the thermoplastic composition was placed directly on the prepared area in the patient's mouth. The thermoplastic composition was cooled with a stream of cold water for about 1 minute. The shell containing the thermoplastic composition was removed from the patient's mouth.

Some of the prostheses were then carefully removed from the shell, trimmed, checked for fit in the mouth, irradiated with a Visilux 2 light for about 5 seconds per unit. Each of these resultant prostheses was then removed from the patient's mouth, further irradiated with a Visilux 2 light for an additional 20 seconds and cemented in place in the patient's mouth using Temp-Bond NE temporary cement.

Others of the prostheses were carefully removed from the shell and irradiated with a Visilux 2 light for about 30 seconds per unit. Each of these resultant prostheses was then checked for fit in the mouth, trimmed and cemented in place in the patient's mouth using Temp-Bond NE temporary cement.

EXAMPLE 20

The composition of EXAMPLE 12 was used as a liner for provisional crowns. The softened thermoplastic composition was independently syringed into a 3M™ Iso-Form™ Crown, a 3M™ Polycarbonate Crown, and a 3M™ Stainless Steel Crown (all from 3M) to fill about two-thirds of each crown. Each crown containing the thermoplastic composition was seated on the prepared tooth, and excess liner expressed around the gingival margins. The liner was allowed to cool approximately 3–4 minutes so that it solidified. Each crown was removed from the prepared area, excess liner was removed from the marginal area by hand tearing. The liner was then irradiated with a Visilux 2 light for 20–30 seconds and cemented in place in the patient's mouth using Temp-Bond NE temporary cement.

EXAMPLE 21

A liner for a provisional crown was fabricated as detailed in EXAMPLE 20, except that after the crown containing the thermoplastic composition was seated on the prepared tooth and excess liner expressed around the gingival margins, the crown containing the thermoplastic composition was cooled in the mouth with a stream of cold water for 30–60 seconds.

EXAMPLE 22

The composition of EXAMPLE 12 was used to prepare a provisional crown. After preparation of the tooth for restorative procedures, the thermoplastic composition was syringed into a metal shell preformed temporary crown (3M™ Iso-Form™ Crown, from 3M) to fill two-thirds of the crown shell. The crown shell containing the thermoplastic composition was then placed over the prepared tooth to form a crown. The thermoplastic composition was cooled in the mouth with a stream of cold water for about 30 seconds.

The metal shell and solidified thermoplastic composition were removed from the prepared area and the marginal excess was removed by hand tearing. The solidified thermoplastic composition crown was then irradiated with a Visilux 2 light for about 30 seconds. The metal shell was removed by making a gingival to occlusal cut with a crown scissors and hand peeling the metal crown from the thermoplastic composition crown. The resultant thermoplastic composition crown was cemented in place in the patient's mouth using Temp-Bond temporary cement.

EXAMPLE 23

A provisional crown was prepared as described in EXAMPLE 22, except that a 3M™ Strip crown (from 3M) was used instead of the metal shell preformed temporary crown.

EXAMPLE 24

A provisional crown was prepared using the procedure of EXAMPLE 23 with the exception that the strip crown was trimmed to the approximate shape of the tooth by removing the tab and cervical areas of the strip crown with a crown scissors.

EXAMPLE 25

The composition of EXAMPLE 12 was independently used to make a provisional crown and bridge using the free-hand technique of the direct method of fabrication. The molten or softened molding composition was syringed onto the lubricated (with petroleum jelly) thumb and forefinger of the practitioner's gloved hand. The thermoplastic composition was transferred to the mouth of the patient and applied directly to the prepared tooth. The thermoplastic composition was shaped over the prepared tooth to fully cover the tooth.

The patient was directed to place the teeth in occlusion. The provisional crown formed of the thermoplastic composition was cooled while the patient's teeth were in occlusion by directing a stream of cold water for about 30 seconds over any accessible areas of the thermoplastic composition crown. The patient was directed to open his mouth and the remainder of the thermoplastic composition crown was cooled with cold water for about 30 seconds.

The crown was removed from the patient's mouth, excess material was removed from the gingival area using a crown scissors and the crown reseated in the patient's mouth to check the fit. The crown was irradiated with a Visilux 2 light for about 30 seconds and cemented in place in the patient's mouth using Temp-Bond NE temporary cement.

EXAMPLE 26

A provisional crown and bridge were independently prepared using the procedure of EXAMPLE 25 with the exception that the thermoplastic composition was syringed directly onto the prepared tooth in the patient's mouth.

EXAMPLE 27

A provisional crown and bridge were independently prepared using the procedure of EXAMPLE 26 with the exception that the procedure was performed on a Typodont model instead of a patient. After the prosthesis was irradiated with a Visilux 2 light for about 30 seconds per unit, a dental burr was used to partially remove cured material on the interior of the prosthesis adjacent to the prepared area. The prosthesis was relined by partially filling the interior of the prosthesis with the thermoplastic composition. The prosthesis was then reseated on the prepared area. The prosthesis was cooled with cold water for about 30 seconds, removed from the Typodont model and the interior of the prosthesis irradiated with a Visilux 2 light for about 10 seconds per unit. The resultant prosthesis was cemented in place on the Typodont model using Temp-Bond NE temporary cement.

EXAMPLE 28

A permanent crown (3M Stainless Steel Crown, from 3M) was lined with the thermoplastic composition of EXAMPLE 12 using the procedure described in EXAMPLE 22, except that the procedure was performed on a Typodont model.

EXAMPLE 29

Four provisional veneers were prepared using the thermoplastic composition of EXAMPLE 12. Two central incisors and two lateral incisors of a Typodont model were prepared for veneers. Four strip crowns were cut down with a crown scissors to leave only the labial surfaces. The thermoplastic composition was syringed onto the interior of the labial surface of each strip crown and seated on the Typodont model.

The strip crowns were cooled with cold water for about 1 minute collectively. The strip crowns containing the thermoplastic composition were removed from the Typodont model. The thermoplastic composition veneers were then removed from the strip crowns and trimmed with a crown scissors. The veneers were irradiated with a Visilux 2 light for about 10 seconds per unit and cemented in place on the Typodont model using Temp-Bond NE temporary cement.

EXAMPLE 30

Inlays and onlays were independently prepared using the thermoplastic composition of EXAMPLE 12 and the procedure of EXAMPLE 17 with the exception that the procedure was performed on a Typodont model instead of a patient.

EXAMPLE 31

The tear strength in the flexible or rubbery stage of the thermoplastic composition of EXAMPLE 12 was measured according to ASTM D624-91 utilizing Die C, except that all linear dimensions, with the exception of sample thickness, were reduced by a factor of one-half. The tear strength of an acrylic-based provisional material, GC Unifast LC Light Quick-Curing Acrylic Resin (from GC Corporation) was also measured. Set out below in TABLE XI are the material, the material type and the tear strength of both materials. The standard deviations are listed in parentheses.

TABLE XI

| Material | Material Type | Tear Strength (Kg/cm) |
| --- | --- | --- |
| Unifast LC | Light-Cured Acrylic | 1.0 (0.4) |
| EXAMPLE 12 | Thermoplastic | 5.0 (0.3) |

The data in TABLE XI show the significantly greater rubbery stage tear strength of the thermoplastic composition of the invention compared to that of a light-cured acrylic material for fabrication of provisional dental prosthetic devices. The high tear strength in the rubbery stage is important insofar as it provides the practitioner the ability to easily remove without tearing the partially cured prosthesis from undercut regions prior to the final set of the material.

EXAMPLE 32

The volumetric shrinkage of the thermoplastic composition of EXAMPLE 12 and five other provisional materials was measured using the method of Puckett and Smith, The Journal of Prosthetic Dentistry, Vol. 68, No. 1, (1992), pp. 56–58. This method measures specific gravity differences between rubbery and cured state specimens. The volumetric shrinkage was measured using the following equation:

$$\% \text{ Shrinkage} = 1 - \frac{\text{Specific Gravity Rubbery} \times 100}{\text{Specific Gravity Cured}}$$

Set out in TABLE XII are the material, the material type, the % shrinkage 1 hour after cure and the % shrinkage 72 hours after cure. The standard deviations are listed in parentheses.

TABLE XII

| Material | Material Type | % Shrinkage 1 Hr. | % Shrinkage 72 Hrs. |
| --- | --- | --- | --- |
| Jet[1] | Self-Cured Acrylic | 5.41 (0.12) | 5.44 (0.12) |
| Unifast LC | Light-Cured Acrylic | 4.34 (0.06) | 4.54 (0.07) |
| Snap[2] | Self-Cured Acrylic | 3.93 (0.03) | 4.12 (0.02) |
| Trim II[3] | Self-Cured Acrylic | 3.88 (0.03) | 3.84 (0.03) |
| Protemp II[4] | Self-Cured Composite | 2.14 (0.03) | 2.65 (0.04) |
| EXAMPLE 12 | Thermoplastic | 2.27 (0.05) | 2.41 (0.95) |

[1] Jet Acrylic, Lang Dental Mfg. Co., Wheeling, IL.
[2] Snap Better Fitting Temporary Crowns and Bridges, Parkell Biomaterials Division, Farmingdale, NY.
[3] Trim II Shade Kit, Bosworth Company, Skokie, IL.
[4] Protemp™ II Temporary Crown & Bridge Material, Espe-Premier, Norristown, PA.

The data in TABLE XII show that the thermoplastic composition of the invention and the self-cured composite exhibited significantly lower volumetric shrinkage than the self-cured and light-cured acrylic materials. Low volumetric shrinkage during and after the fabrication procedure is important insofar as it provides provisional prosthetic devices that more accurately replicate the dental area that is being restored and thus provide better fitting interim restorations.

EXAMPLE 33

Provisional prosthetic devices were fabricated by five dental practitioners using the thermoplastic composition of the invention and commercially available provisional fabrication products. Both the thermoplastic composition of the invention and the provisional material generally utilized by the practitioner were independently used to fabricate a temporary restoration on the same tooth preparation in a patient's mouth.

Set out in TABLE XIII are the patient no., the prosthesis type, the method/technique of fabrication used, the material, the time to place up to finishing/polishing and the concurrent time savings and the time to finish/polish up to seating and the time difference between the thermoplastic composition and the provisional fabrication product, either acrylic or resin based composite, utilized by the practitioner.

TABLE XIII

| Patient No. | Prosthesis Type | Method/Technique | Material | Time to Place (Up to F/P[1]) | Time Savings | Time to F/P (Up to Seating) | Time Savings |
| --- | --- | --- | --- | --- | --- | --- | --- |
| 1 | 6 Adjacent Crowns | Direct/Free-Hand | Jet Acrylic | 6 Min. 20 Sec. | 2 Min. 50 Sec. | 17 Min. 0 Sec. | 3 Min. 0 Sec. |
|   |   |   | EXAMPLE 12 | 3 Min. 30 Sec. |   | 14 Min. 0 Sec. |   |
| 2 | Crown | Direct/In Alginate Impression | Protemp | 4 Min. 10 Sec. | 1 Min. 40 Sec. | 2 Min. 50 Sec. | 25 Sec. |
|   |   |   | EXAMPLE 12 | 2 Min. 30 Sec. |   | 2 Min. 25 Sec. |   |
| 3 | Crown | Direct/In Alginate Impression | Jet Acrylic | 7 Min. 20 Sec. | 3 Min. 10 Sec. | 5 Min. 10 Sec. | 40 Sec. |
|   |   |   | EXAMPLE 12 | 4 Min. 10 Sec. |   | 4 Min. 30 Sec. |   |
| 4 | Crown | Direct/In PVS[2] Impression | Snap | 7 Min. 0 Sec. | 3 Min. 25 Sec. | 2 Min. 0 Sec. | 1 Min. 40 Sec. |
|   |   |   | EXAMPLE 12 | 3 Min. 35 Sec. |   | 0 Min. 20 Sec. |   |
| 5 | 3 Unit Bridge | Direct/In PVS[2] Impression | Snap | 5 Min. 0 Sec. | 1 Min. 0 Sec. | 4 Min. 0 Sec. | 0 Sec. |
|   |   |   | EXAMPLE 12 | 4 Min. 0 Sec. |   | 4 Min. 0 Sec. |   |
| 6 | Crown | Direct/In PVS Impression | Snap | 6 Min. 0 Sec. | 1 Min. 0 Sec. | 2 Min. 30 Sec. | 0 Sec. |
|   |   |   | EXAMPLE 12 | 5 Min. 0 Sec. |   | 2 Min. 30 Sec. |   |
| 7 | Crown | Direct/In PVS Impression | Snap | 6 Min. 45 Sec. | 1 Min. 35 Sec. | 2 Min. 45 Sec. | −1 Min. 25 Sec. |
|   |   |   | EXAMPLE 12 | 5 Min. 10 Sec. |   | 4 Min. 10 Sec. |   |

TABLE XIII-continued

| Patient No. | Prosthesis Type | Method/Technique | Material | Time to Place (Up to F/P[1]) | Time Savings | Time to F/P (Up to Seating) | Time Savings |
|---|---|---|---|---|---|---|---|
| 8 | Crown | Direct/In PVS Impression | Snap EXAMPLE 12 | 7 Min. 40 Sec. 3 Min. 50 Sec. | 3 Min. 50 Sec. | 6 Min. 10 Sec. 10 Min. 20 Sec. | −3 Min. 70 Sec. |
| 9 | 3 Unit Bridge | Direct/In Alginate Inpression | Pro Temp EXAMPLE 12 | 6 Min. 0 Sec. 5 Min. 5 Sec. | 55 Sec. | 11 Min. 50 Sec. 11 Min. 17 Sec. | 33 Sec. |
| 10 | Crown Liner | Using Iso-Form Crown | Jet Acrylic EXAMPLE 12 | 6 Min. 20 Sec. 0 Min. 50 Sec. | 5 Min. 30 Sec. | 2 Min. 0 Sec. 2 Min. 0 Sec. | 0 Sec. |

[1]Time to place the prosthesis up to finishing/polishing from the time of syringing the material through light curing for EXAMPLE 12 and from the time of dispensing the composition components through complete set for the commercially available provisional materials.
[2]Polyvinylsiloxane The data in TABLE XIII show the time savings generally provided by the use of the thermoplastic composition of the invention. In all instances when using the thermoplastic composition, there was a time savings in terms of amount of time required to place the provisional restoration up to finishing/polishing. Only in the case of patient nos. 3 and 4 did it require more time to finish/polish the provisional thermoplastic composition restoration compared to finishing/polishing the provisional restoration fabricated using a commercially available provisional material.

Although this invention has been described using certain illustrative examples, it should be understood that the invention is not limited to the specific exemplary embodiments shown in this specification.

What is claimed:

1. A dental crown having a dental crown liner made from a molding composition comprising a thermoplastic material, the uncured molding composition being solid at 38° C. and having a melting or softening point that comfortably can be withstood by oral tissues.

2. A dental crown according to claim 1, wherein the molding composition comprises a free-radically polymerizable resin.

3. A dental crown according to claim 2, wherein the liner is used in combination with a provisional crown.

4. A dental crown according to claim 2, wherein the free-radically polymerizable resin comprises an acrylate or methacrylate.

5. A dental crown according to claim 2, wherein the free-radically polymerizable resin comprises an unsaturated amide.

6. A dental crown according to claim 2, wherein the free-radically polymerizable resin comprises an acrylated urethane oligomer or polymer.

7. A dental crown according to claim 2, wherein the free-radically polymerizable resin comprises an acrylated polyester oligomer or polymer.

8. A dental crown according to claim 1, wherein the molding composition comprises a blend of a thermoplastic material and a free-radically polymerizable resin.

9. A dental crown according to claim 1, wherein the dental crown liner is used in combination with a provisional crown.

10. A dental crown according to claim 1, wherein the thermoplastic material comprises a polyester or a polyurethane.

11. A dental crown according to claim 10, wherein the polyester comprises a segmented polyester.

12. A dental crown according to claim 1, wherein the thermoplastic material comprises a polycaprolactone.

13. A dental crown according to claim 12, wherein the polycaprolactone has the formula:

where $R^1$ is an aromatic or a straight chain or branched aliphatic backbone, w is 1 if $R^1$ is hydrogen, and w otherwise has an average value from about 1 to about 4, M is oxygen or —$NR^2$— where $R^2$ is hydrogen or a non-interfering aromatic or aliphatic group, and the product of w times x is greater than about 35.

14. A dental crown according to claim 1, wherein the molding composition further comprises a photoinitiator.

15. A dental crown liner made from a molding composition comprising a thermoplastic material, the uncured molding composition being solid at 38° C. and having a melting or softening point that comfortably can be withstood by oral tissues.

16. A dental crown liner according to claim 15, wherein the molding composition comprises a free-radically polymerizable resin.

17. A dental crown liner according to claim 16, wherein the liner is used in combination with a provisional crown.

18. A dental crown liner according to claim 16, wherein the free-radically polymerizable resin comprises an acrylate or methacrylate.

19. A dental crown liner according to claim 16, wherein the free-radically polymerizable resin comprises an unsaturated amide.

20. A dental crown liner according to claim 16, wherein the free-radically polymerizable resin comprises an acrylated urethane oligomer or polymer.

21. A dental crown liner according to claim 16, wherein the free-radically polymerizable resin comprises an acrylated polyester oligomer or polymer.

22. A dental crown liner according to claim 15, wherein the molding composition comprises a blend of a thermoplastic material and a free-radically polymerizable resin.

23. A dental crown liner according to claim 15, wherein the dental crown liner is used in combination with a provisional crown.

24. A dental crown liner according to claim 15, wherein the thermoplastic material comprises a polyester or a polyurethane.

25. A dental crown liner according to claim 24, wherein the polyester comprises a segmented polyester.

26. A dental crown liner according to claim 15, wherein the thermoplastic material comprises a polycaprolactone.

27. A dental crown liner according to claim 26, wherein the polycaprolactone has the formula:

where $R^1$ is an aromatic or a straight chain or branched aliphatic backbone, w is 1 if $R^1$ is hydrogen, and w otherwise has an average value from about 1 to about 4, M is oxygen or —$NR^2$— where $R^2$ is hydrogen or a non-interfering aromatic or aliphatic group, and the product of w times x is greater than about 35.

28. A dental crown liner according to claim 15, wherein the molding composition further comprises a photoinitiator.

* * * * *